US012797210B2

(12) United States Patent
Bouma et al.

(10) Patent No.: US 12,797,210 B2
(45) Date of Patent: Nov. 17, 2026

(54) METHOD OF DESIGNING AND MANUFACTURING AN ELASTIC CIRCUMFERENTIAL RIM OF A PROSTHETIC OR ORTHOTIC DEVICE

(71) Applicant: Invent Medical Group, s.r.o., Ostrava (CZ)

(72) Inventors: Tomas Bouma, Rychvald (CZ); Ales Grygar, Koprivnice (CZ); Jiri Rosicky, Frydlant (CZ)

(73) Assignee: Invent Medical Group, s.r.o., Ostrava (CZ)

( * ) Notice: Subject to any disclaimer, the term of this patent is extended or adjusted under 35 U.S.C. 154(b) by 203 days.

(21) Appl. No.: 18/863,433

(22) PCT Filed: May 2, 2023

(86) PCT No.: PCT/CZ2023/050024
§ 371 (c)(1),
(2) Date: Nov. 6, 2024

(87) PCT Pub. No.: WO2023/213337
PCT Pub. Date: Nov. 9, 2023

(65) Prior Publication Data

US 2025/0360004 A1 Nov. 27, 2025

(30) Foreign Application Priority Data

May 6, 2022 (CZ) ................................ CZ2022-190

(51) Int. Cl.
*A61F 2/50* (2006.01)
*A61F 2/30* (2006.01)
(Continued)

(52) U.S. Cl.
CPC .............. *A61F 2/5046* (2013.01); *A61F 2/30* (2013.01); *A61F 2/7812* (2013.01); *A61F 2/80* (2013.01);
(Continued)

(58) Field of Classification Search
CPC ..................................................... A61F 2/5046
(Continued)

(56) References Cited

U.S. PATENT DOCUMENTS

2004/0260402 A1 12/2004 Baldini et al.
2010/0204816 A1 8/2010 Sabiston
(Continued)

FOREIGN PATENT DOCUMENTS

EP 3049035 A1 8/2016
WO 2021262152 A1 12/2021

OTHER PUBLICATIONS

European Patent Office, International Search Report, dated Jul. 7, 2023, in International Patent Applicaiton No. PCT/CZ2023/050024, filed on May 2, 2023.
(Continued)

*Primary Examiner* — Travis R Hunnings
(74) *Attorney, Agent, or Firm* — Thedford I. Hitaffer; Hitaffer, PLLC

(57) ABSTRACT

A method of designing and manufacturing an elastic circumferential rim of a prosthetic or orthotic device includes a step of creating a basic structure of the elastic circumferential rim based on the type of the prosthetic or orthotic device. Requirements are determined for stiffness of the elastic circumferential rim in the individual areas along the circumference of the elastic circumferential rim. A structural model of the elastic circumferential rim is created based on the requirements for stiffness of the elastic circumferential rim in the individual areas along the circumference of the
(Continued)

elastic circumferential rim and the basic structure of the elastic circumferential rim. The elastic circumferential rim is manufactured based on the structural model of the elastic circumferential rim.

8 Claims, 6 Drawing Sheets

(51) Int. Cl.
*A61F 2/78* (2006.01)
*A61F 2/80* (2006.01)
*B33Y 10/00* (2015.01)

(52) U.S. Cl.
CPC ..... *B33Y 10/00* (2014.12); *A61F 2002/30069* (2013.01); *A61F 2002/505* (2013.01)

(58) Field of Classification Search
USPC .............................................................. 700/98
See application file for complete search history.

(56) References Cited

U.S. PATENT DOCUMENTS

| | | | | |
|---|---|---|---|---|
| 2015/0165690 | A1* | 6/2015 | Tow | B33Y 10/00 700/119 |
| 2016/0374431 | A1* | 12/2016 | Tow | A43D 1/022 36/43 |
| 2018/0368996 | A1 | 12/2018 | Van Vliet et al. | |
| 2022/0071780 | A1* | 3/2022 | Seifert | A61F 2/72 |

OTHER PUBLICATIONS

European Patent Office, Written Opinion, dated Jul. 7, 2023, in International Patent Applicaiton No. PCT/CZ2023/050024, filed on May 2, 2023.

* cited by examiner

METHOD OF DESIGNING AND MANUFACTURING AN ELASTIC CIRCUMFERENTIAL RIM OF A PROSTHETIC OR ORTHOTIC DEVICE

CROSS-SECTION TO RELATED APPLICATION

This application, filed under 35 USC 371, is a United States National Stage Application of International Application No. PCT/CZ2023/050024, filed May 2, 2023, which claims priority to CZ PV 2022-190, filed May 6, 2022, the disclosures of which are incorporated herein by reference in their entirety.

FIELD OF THE INVENTION

The invention relates to a method of designing and manufacturing an elastic circumferential rim of a prosthetic or orthotic device, in particular the elastic circumferential rims of the prosthetic sockets, upper or lower limb orthoses, cranial orthoses, trunk orthoses.

BACKGROUND OF THE INVENTION

In the field of prosthetic and orthotic devices, more and more emphasis is placed on the comfort of the device user, wherein new technologies, in particular a 3D printing, have made it possible to move the possibilities of providing the comfort of prosthetic and orthotic devices to a higher level. Based on the evaluation of many different information about the user, including the specification of his disability, it is possible to create a tailor-made prosthetic or orthotic device to functionally fulfil its function while maintaining maximum comfort of the patient.

While the majority of the development in the field is concerned with the optimalization of the prosthetic or orthotic device on the contact regions of the user's body, regarding its edge, the current solutions of the tailor-made devices are very simple, straightforward and do not take into account the anatomy and physiology of the user's body.

Most of the current solutions of the elastic circumferential rims of the tailor-made devices are designed very simply, wherein they have a constant cross-section along the entire circumference and only surround the edge of the rigid shell of the prosthetic or orthotic device.

Some of the already known solutions represent more complex embodiments of the flexible circumferential rims, which take into account the basic anatomy of the users body in the application site of the prosthetic or orthotic device. Such solution is disclosed for example in document EP3049035A1, where the upper peripheral rim of the anterior part of the ankle joint orthosis is higher in the middle of its width, or the peripheral rim has a larger cross-section in the middle of its width, which makes it more bendable in this place. This stretcher area on the upper rim ensures a sufficient space for the fibula while maintaining partial support when walking. The peripheral rim solution disclosed in the document takes into account the basic human anatomy, but it does not consider other variables linked to the specific user which would further increase the comfort of the peripheral rim with regard to not only the general human anatomy but also the anatomy and physiology of the specific user or the specific dimensions of the device for this user for whom the device is intended.

The above-mentioned reasons imply that it is desirable to develop a process of designing and manufacturing the elastic peripheral rim of the tailor-made prosthetic or orthotic device which would adapt the elastic rim in different areas along its circumference to the contact areas on the specific users body with regard to the anatomic and physiologic specifics of the user and/or the specific types and dimensions of the prosthetic or orthotic device.

SUMMARY OF THE INVENTION

The above-mentioned drawbacks are eliminated to a certain extent by a method of designing and manufacturing an elastic circumferential rim of a prosthetic or orthotic device including the following steps of:

a) creating a basic structure of the elastic circumferential rim based on the type of the prosthetic or orthotic device,
b) determining the requirements for stiffness of the elastic circumferential rim in the individual areas along the circumference of the elastic circumferential rim based on the dimensions of the prosthetic or orthotic device or at least one data on the device user,
c) creating a structural model of the elastic circumferential rim based on the requirements for stiffness of the elastic circumferential rim in the individual areas along the circumference of the elastic circumferential rim and the basic structure of the elastic circumferential rim, wherein the stiffness of the elastic circumferential rim in the individual areas along the circumference of the elastic circumferential rim is adjusted by at least one parameter of the set including rim height, rim thickness, rim thickness gradient depending on rim height,
c) manufacturing the elastic circumferential rim based on the structural model of the elastic circumferential rim.

The main advantage of this method is optimization of the rim stiffness in the individual areas along its circumference to the specific user to ensure his comfort while maintaining the maximal functionality of the prosthetic or orthotic device. The method of the invention further allows optimization of the plurality of the used material for the manufacture of the elastic circumferential rim, since adjustment of its geometry is adapted to the specific user, and therefore only as much material as is needed is used for its manufacture.

In the preferred embodiment, the step of manufacturing the elastic circumferential rim is performed by a 3D printing technology. With the 3D printing technology, the elastic circumferential shape can be precisely tailored quickly and without waste residual material.

Preferably, the elastic circumferential rim is made of elastomer. Elastomers are preferred materials for the rim, since their stiffness can be easily affected even by small changes in the part geometry.

Preferably, the step of determining the requirements for stiffness of the elastic circumferential rim includes the steps of determining the position of the elastic circumferential rim on the users body and a following step of determining the area stiffness of the elastic circumferential rim. Preferably, the step of determining the position of the elastic circumferential rim on the user's body performed based on the dimensions of the prosthetic and orthotic device and the step of determining the area stiffness of the elastic circumferential rim performed based on the position of the elastic circumferential rim on the user's body and at least one data on the device user are used. The optimal stiffness in the given rim area should be adjusted to the user's body area with which it is in contact, therefore, it is firstly preferred to determine the precise rim position and then to determine the stiffness of the given area. The precise rim position should only be determined based on the precise dimensions of the device, wherein the area stiffness is preferably adjusted both based on the position and information about the user.

In preferred embodiments, the requirements for stiffness of the elastic circumferential rim in the individual areas along the circumference of the elastic circumferential rim are determined based on data on the device user including the tissue specifics of user's body part intended for the prosthetic or orthotic device and at least one data on the overall user status of the set of user's age, users weight, user's height, users activity. For the maximal comfort of the user, the tissue specifics in the given user's body part, thus the disability specifics, and also the overall user status should be taken into account.

Preferably, the stiffness of the elastic circumferential rim in the individual areas along the circumference of the elastic circumferential rim is adjusted by the rim thickness gradient depending on rim height. With the rim thickness gradient depending on rim height, it is possible to adjust the rim stiffness to the requirements for stiffness in the most precise way.

Preferably, the stiffness adjustment of the elastic circumferential rim in the individual areas along the circumference of the elastic circumferential rim by the rim thickness parameter includes a step of implementing a cavity into at least one area along the circumference of the elastic circumferential rim. This reduces the area stiffness ("softening") and at the same time saves the material.

DESCRIPTION OF THE DRAWINGS

The summary of the invention is further clarified by the examples of its embodiments, which are described using the attached drawings, in which.

EXEMPLARY EMBODIMENTS OF THE INVENTION

Figure 1:
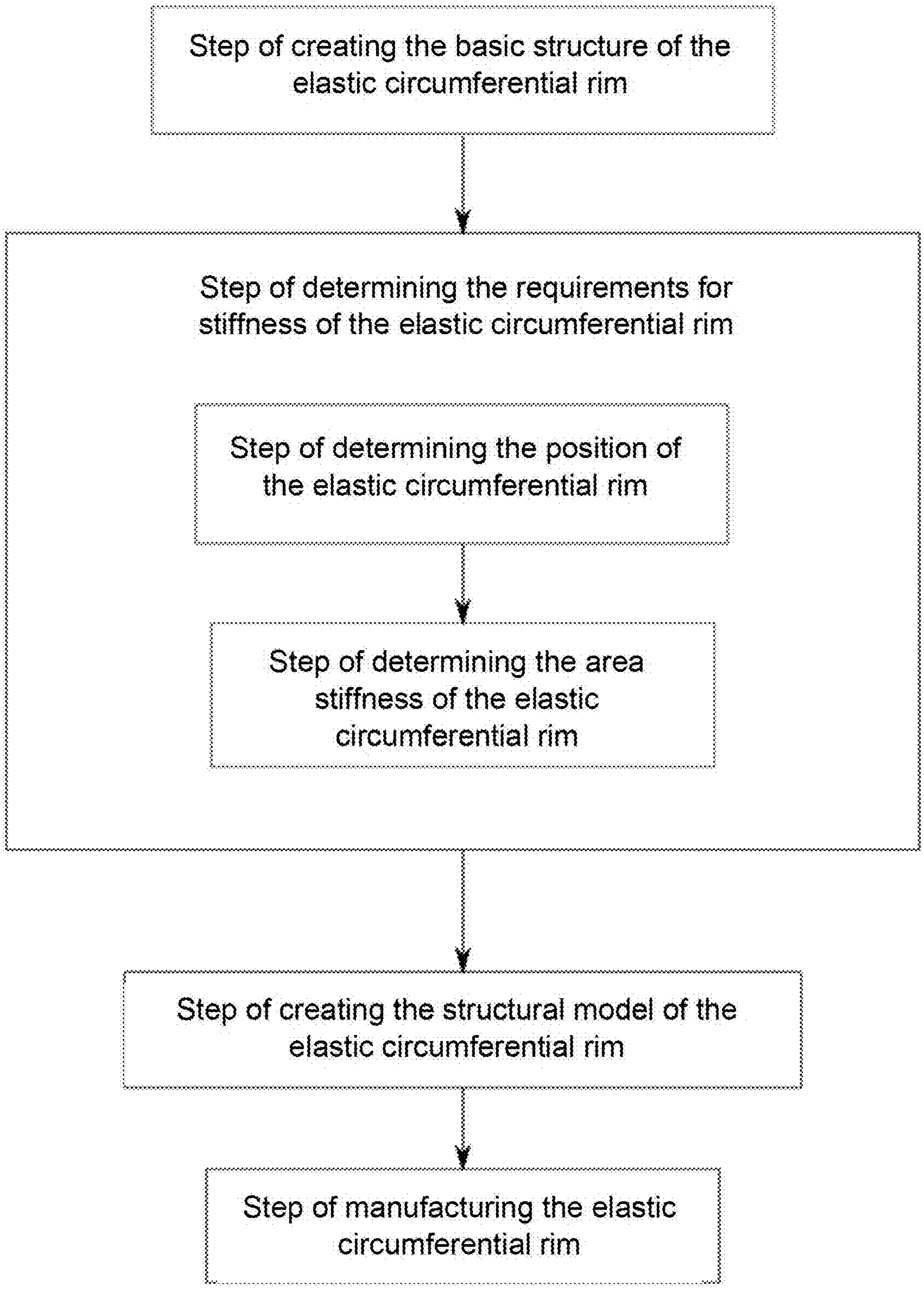
FIG. 1 shows the method of designing and manufacturing the elastic circumferential rim of the prosthetic or orthotic device according to the first exemplary embodiment.
Figure 2:
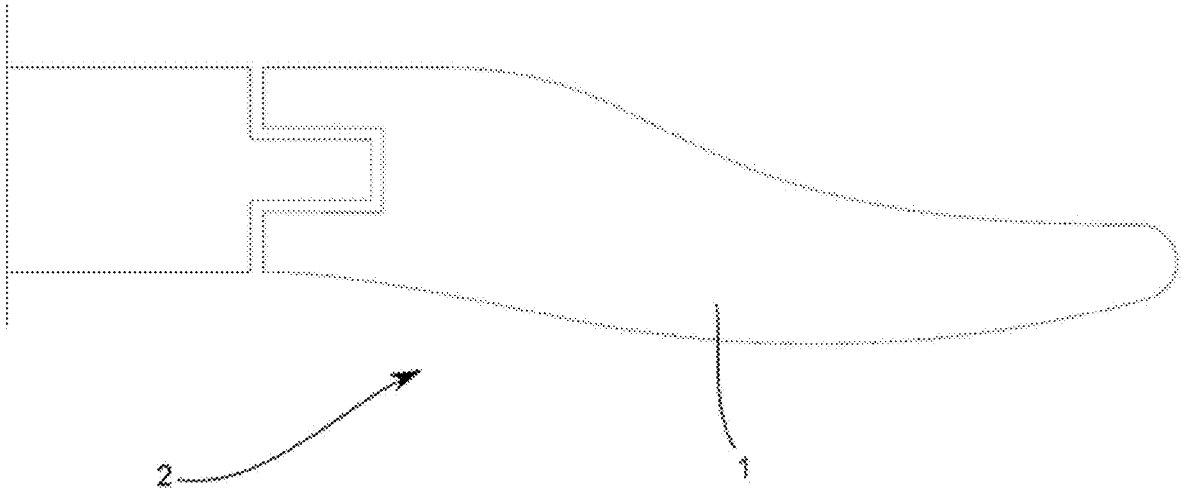
FIG. 2 shows a cross-section of the elastic circumferential rim according to the first exemplary embodiment of the invention with default rim stiffness.
Figure 3:
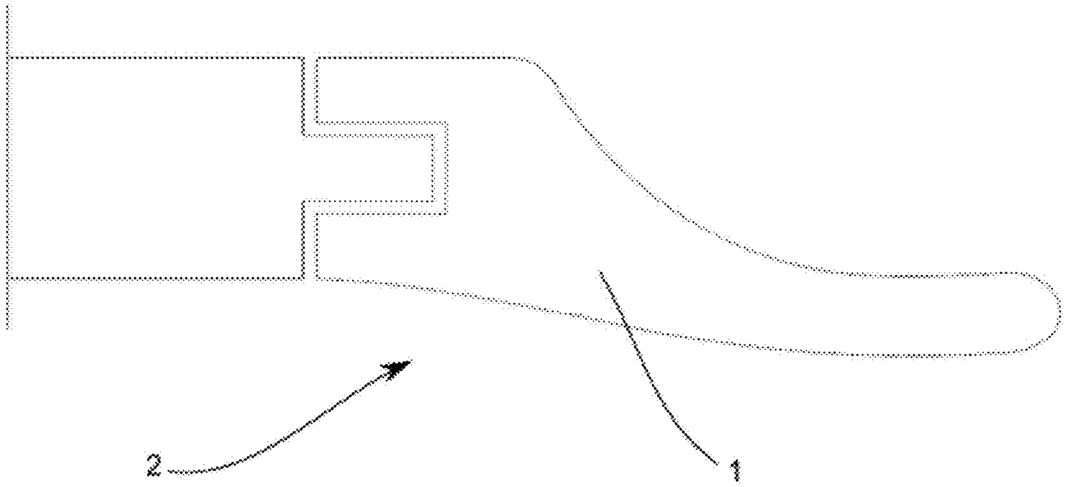
FIG. 3 shows a cross-section of the elastic circumferential rim according to the first exemplary embodiment of the invention with reduced stiffness compared to default rim stiffness by adjusting the rim thickness parameter.
Figure 4:
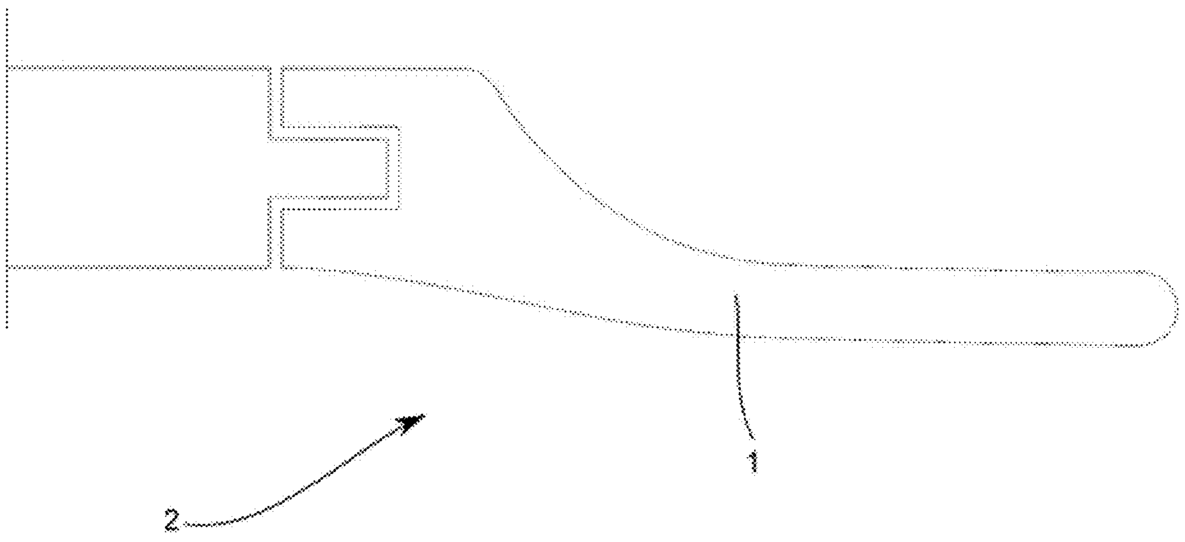
FIG. 4 shows a cross-section of the elastic circumferential rim according to the first exemplary embodiment of the invention with reduced stiffness compared to default rim stiffness by adjusting both the rim height and the rim thickness parameters.
Figure 5:
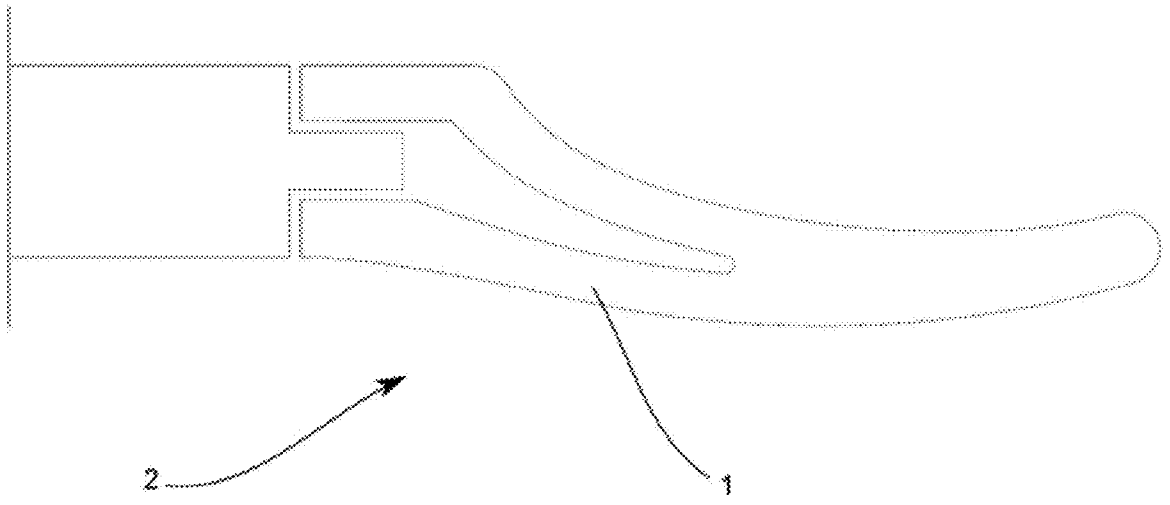
FIG. 5 shows a cross-section of the elastic circumferential rim according to the first exemplary embodiment of the invention with reduced stiffness compared to default rim stiffness by adjusting both the rim height and the rim thickness parameters with implementation of the cavity into the rim.

Some terms used in the description below will be clarified herein. The prosthetic and orthotic devices 2 (also referred to as devices 2) refer in the context of the invention to medical devices which are adapted to be attached to the users body and be in contact with the user's body. The elastic circumferential rim 1 of the prosthetic or orthotic device 2 (also referred to as rim 1) refers to a segment which forms an elastic edge of the prosthetic or orthotic device 2 along at least part of its circumference, and thus also along at least part of the circumference of the user's body, for example along the circumference of his limb. The circumference of the prosthetic or orthotic device 2 refers to the outermost contour of the prosthetic or orthotic device 2 lining its edges above the surface of the user's body. The circumferential rim 1 refers to the rim with which at least part of the circumference of the prosthetic or orthotic device 2 is provided. The rim 1 height refers to its dimension by which the elastic rim 1 extends the rigid shell of the prosthetic or orthotic device 2 in the direction perpendicular to the edge of the rigid shell of the prosthetic or orthotic device 2, that is the rim dimension in the direction parallel to the surface of the user's body, wherein the rim 1 height has usually a value from 0.5 to 5 cm, in particular 1 to 3 cm. The boundary between the elastic circumferential rim 1 and the rigid shell is defined by a line where the wall properties of the prosthetic or orthotic device 2 change abruptly from the substantially stiff and rigid shell to the flexible peripheral part. The rim 1 thickness refers to a thickness of the rim 1 wall, that is the rim 1 dimension in the direction perpendicular to the surface of the user's body. The rim 1 thickness gradient depending on rim 1 height refers to a change in rim 1 thickness depending on its height, wherein the gradient thus determines how the rim 1 thickness changes at different levels of its height.

The stiffness refers to a degree of reversible deformation under the action of external force. The circumferential rim 1 is from an elastic and stretchy material and its irreversible deformations are undesirable. If the rim 1 area has a higher stiffness, it is understood that under the action of the same acting force, the rim 1 in this area is less irreversibly deformed than in the areas with lower stiffness, or with higher elasticity. The stiffness of the circumferential rim 1 in the specific area is measured under the action of the force from the inner side of the rim 1 in the direction perpendicular to the surface of the users body in the highest point of the rim 1, wherein the result is the difference of the distances between the position of this point in the undeformed and deformed state in the direction perpendicular to the surface of the user's body. For example, the statement that the rim 1 stiffness is 20% smaller in the first rim 1 area than in the second rim 1 area refers to the fact that under the same size of the acting force, the difference of the distances in the first rim 1 area was measured 20% bigger compared to the measured difference of the distance in the second rim 1 area. The acting force refers to a force of size from the range of forces to which the elastic rim 1 is exposed as a standard in the individual prosthetic or orthotic devices 2.

The dimensions of the prosthetic or orthotic device 2 refer to any information defining the size and shape of the prosthetic or orthotic device 2, those include its height, width, thickness, roundness, circumference but also for example its 3D model. These dimensions determine in which places the peripheral rim 1 will be in contact with user's body. Even based on the type of the prosthetic or orthotic device 2, it is already apparent approximately where the peripheral rim 1 will be located or where the rim 1 will be in contact with the user and what its dimensions will be, as it largely predetermines the dimensions of the prosthetic or orthotic device 2. The type of the prosthetic or orthotic device 2 also specifically determines for which user's body part the device 2 is intended and for what purpose. The types of the prosthetic and orthotic devices 2 include a transtibial prosthetic socket, transfemoral prosthetic socket, supramalleolar orthosis, ankle joint orthosis, knee orthosis, hip orthosis, wrist orthosis, elbow orthosis, shoulder orthosis, neck orthosis, cranial orthosis, trunk orthosis, etc., the type of the prosthetic or orthotic device 2 can however be a separate part of the orthosis or prosthesis, such as a flexible inner liner of the prosthetic socket, anterior flexible part of an ankle joint orthosis, flexible parts in the ankle area of an ankle joint orthosis, inner flexible shell of the cranial orthosis.

Data on the device 2 user are divided into 3 categories: data on the overall user status, data on the dimensions of the users body part and specifics of the user's body part for which the device 2 is intended. Data on the overall user status represent the overall characteristics of the user, which are age, height, weight, and the level of activity.

Data on the dimensions of the user's body part refer to any information about the user, which affect the dimensions and shape of the prosthetic or orthotic device 2 and shape and position of its rim 1, for example a 3D model of the user's body part; the dimension parameters of the residual limb, in particular the distance of the mid-patellar ligament (MPT) from the ground, knee joint pitch and circumference, residual limb length; the lower limb dimensions, in particular foot size, pitch and circumference across the knee joint, distance in the direction of the longitudinal axis of the sole between the furthest point of the sole heel and the metatarsal head of the little finger, the distance in the direction of the longitudinal axis of the sole between the furthest point of the sole heel and the metatarsal head of the thumb, sole width at the point between the metatarsal head of the little finger and the metatarsal head of the thumb, sole width at the heel, ankle pitch, pitch above ankles and ankle height; the upper limb dimensions, in particular palm circumference, forearm circumference, upper arm circumference, length of the longest finger, arm length, forearm length, upper arm length, palm pitch, wrist pitch, forearm pitch; the head dimensions, in particular head circumference, longitudinal dimension (AP), transverse dimension (ML).

The tissue specifics of the users body part represent any information about the tissue status in the user's body part for which the device 1 is intended, which affect the desired stiffness of the device 2 in the individual contact areas with the users body, for example, disability specifics of the user's body part, location of the soft tissues, bone prominences, sensitive places, neural pathways or vascular supply; the residual limb specifics such as flexion, abduction or adduction, external and internal rotation; the residual limb type (muscular, normal, atrophied, bony); the range of motion in the knee and hip joints.

With regard to their nature, the prosthetic and orthotic devices 2 are tailor-made, wherein during their design and manufacture, several variables must be taken into account to fulfil their function while maintaining as much comfort as possible for the specific user, wherein for each user the resulting device 2 is different. The process of designing and manufacturing the elastic circumferential rim 1 of the device 2 is also similarly affected. The process of designing and manufacturing the elastic circumferential rim 1 is closely related to a process of designing and manufacturing the prosthetic or orthotic device 2, since the rim 1 is for obvious reasons dependent on the specification of the respective device 2 and its purpose.

The process of designing and manufacturing the elastic circumferential rim 1 can be completely implemented into the process of designing and manufacturing the prosthetic or orthotic device 2, wherein the input can be the same input data, which are used in designing the prosthetic and orthotic device 2 itself, that is data on the device 2 user, as well as the manufacture can take place simultaneously or within one process. For example, the manufacture can be performed using a single-material 3D printing or multi-material 3D printing, where both the shell of the prosthetic or orthotic device 2 made of one material and the elastic circumferential rim 1 made of another stretcher material are made during one manufacturing cycle, these materials can have sufficient adhesion to each other, alternatively they can already be printed with a shaped lock or can be provided with another connection element.

In another embodiment, the elastic rim 1 can be made of the same material as the prosthetic or orthotic device 2, wherein the difference in the elasticity between the shell and the circumferential rim 1 can be ensured by a step change in thickness, or device 2 thickness gradient in the rim 1 area. In such embodiment, the prosthetic or orthotic device 2 has thus generally increased elasticity compared to the rest of the shell, wherein the different values of the rim 1 stiffness along the circumference of the rim 1 are ensured by different thickness, length, and rim 1 thickness gradient depending on rim 1 height along the circumference of the rim 1.

The process of designing the elastic circumferential rim 1 according to the first exemplary embodiment of the invention takes place on the computer device in a software interface, wherein its diagram is shown in FIG. 1. The process of designing the elastic circumferential rim 1 according to the first exemplary embodiment of the invention begins with the step of creating the basic structure of the elastic circumferential rim 1 based on the type of the prosthetic or orthotic device 2. Based on the type of the prosthetic or orthotic device 2, the default rim 1 stiffness and the rim 1 location are determined, that is which edges of the prosthetic or orthotic device 2 will be provided with the rim 1, from which the rim length and its basic shape following the contours of the device 2 are thus determined. The default rim 1 stiffness is a stiffness which the rim 1 has before any stiffness adjustments based on the input parameters discussed here (type of the prosthetic or orthotic device 2, their dimensions, or data on the device user) and which the rim 1 has in the areas where the rim 1 stiffness is not adjusted in any way or where its height, width, rim 1 thickness gradient are not adjusted. It can therefore be said that the default state of the design of the circumferential rim 1 according to the invention is a rim 1 with a constant cross-section and default stiffness along its entire length, which is determined by the type of the device 2. The default rim 1 stiffness in the first exemplary embodiment represents the highest value of the rim 1 stiffness which is in the individual areas reduced based on the rim 1 position and data on the device 2 user.

The next step is determining the requirements for rim 1 stiffness in the individual areas along the circumference of the rim 1, the one in the first exemplary embodiment includes the steps of determining the rim 1 position on the users body, thus establishing the users body part with which the circumferential rim 1 will be in contact, and the step of determining the area stiffnesses of the rim 1, which includes the step of determining the rim 1 areas, where the rim 1 is divided into areas, wherein in the step of determining the area stiffnesses of the rim 1, the requirements for stiffness in the individual areas along the circumference of the rim 1 defined in the step of determining the areas on the user's body are determined.

In the step of determining the rim 1 position on the user's body, it is defined, based on the specific dimensions of the prosthetic or orthotic device 2, in which precise areas the circumferential rim 1 of the device 2 will be in contact with the user's body. The dimensions of the prosthetic or orthotic device 2 are determined based on the already known shape and size of the user's body part for which the device 2 is intended, wherein the dimensions of the prosthetic or orthotic device 2 also represent indirect information about the dimensions of the users body. In the first exemplary embodiment, the dimensions of the prosthetic or orthotic device 2 are the 3D model of the prosthetic or orthotic device 2, wherein the precise areas with which the circumferential rim 1 of the device 2 is in contact are determined by comparison of the 3D model of the prosthetic or orthotic device 2 with the 3D model of the user's body part. For some types of the prosthetic or orthotic device 2, it is possible to define these areas without comparison since the areas with which the rim 1 is in contact are able to be determined by the one skilled in the art without comparison with the model of the users body. For more precise determination of the rim 1 position, it is however preferred to compare the model of the device 2 with the user's body directly. In other embodiments, the already made prosthetic or orthotic device 2 can be compared directly with the user's body part, for example by putting it on the users body, for this purpose, the artificial model of the users body part can also be used.

The step of determining the area stiffnesses of the rim 1 follows, which begins with the step of determining the rim 1 areas, where the rim 1 is divided into the individual rim 1 areas. The rim 1 area along the circumference of the rim 1 refers to an area of the rim 1 part which is defined based on the characteristics of the user's body areas to which it abuts in the resting state and while moving. Preferably, the rim 1 is firstly divided into parts along the length of the rim 1 and each rim 1 part thus forms a part of the circumference of the rim 1. More parts the rim 1 is divided into, more precisely it is possible to adapt the rim 1 areas to the characteristic areas on the user's body. In the first exemplary embodiment, the rim 1 is divided in such way that each its part forms 1 mm of the circumference of the rim. In other embodiments, the resolution can be 0.1 mm to 2 cm of the circumference of the rim 1 per one rim 1 part. The rim 1 area is then a group of these rim 1 parts corresponding to the characteristic areas on the users body. The rim 1 parts can be part of even more than one rim 1 area.

Based on the rim 1 position itself and based on the knowledge of the human body anatomy, the rim 1 areas corresponding to the sensitive areas of the users body are determined. It is clear from human anatomy, where on the body the sensitive areas are located, in particular bones and bone protrusions, courses of the blood vessels, nerves, attachments, etc. Within the examples of the embodiments of the step of determining the rim 1 areas according to the invention, the following examples indicate a common location of the rim 1 on the standard types of the prosthetic or orthotic devices 2. In the following examples of the devices 2, the typical areas where the rim 1 of the specific device 2 usually extends are provided with the selection of rim 1 areas where the rim 1 stiffness is preferably reduced due to the occurrence of the sensitive areas of the user's body.

Figure 6:
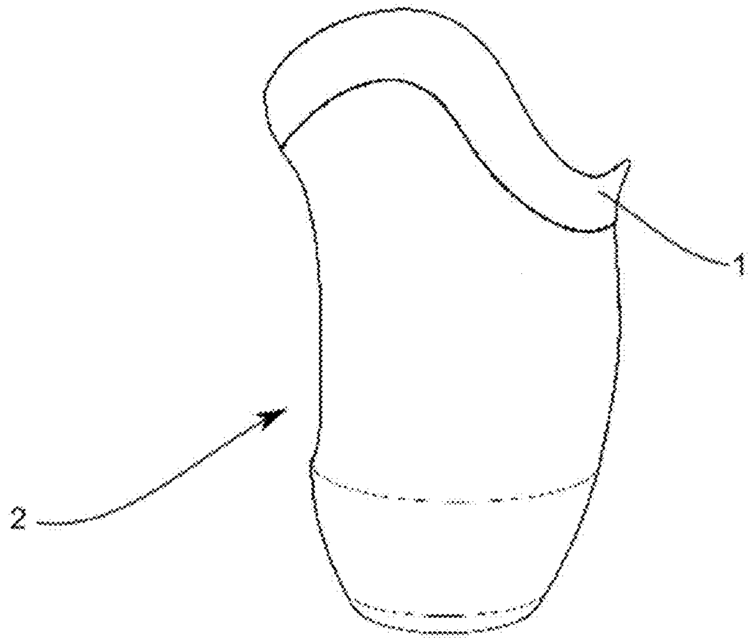
FIG. 6 shows the transtibial prosthetic socket with the elastic circumferential rim according to the invention.
Figure 7:
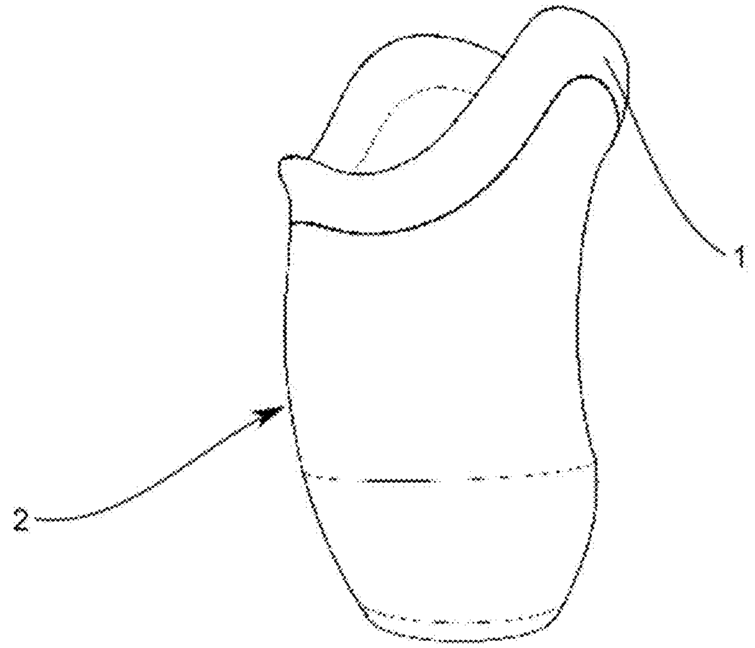
FIG. 7 shows the transtibial prosthetic socket with the elastic circumferential rim according to the invention.

Transtibial prosthetic socket (shown in FIG. 6 and FIG. 7)—the elastic circumferential rim 1 is in contact with the user's lower limb in the areas of the knee joint patella, femoral condyles, hamstring attachments and popliteal fossa, wherein the areas of the elastic rim 1 with reduced stiffness are mostly located in the area of the posterior socket part, i.e., in the area of the hamstring attachments and popliteal fossa.

Figure 8:
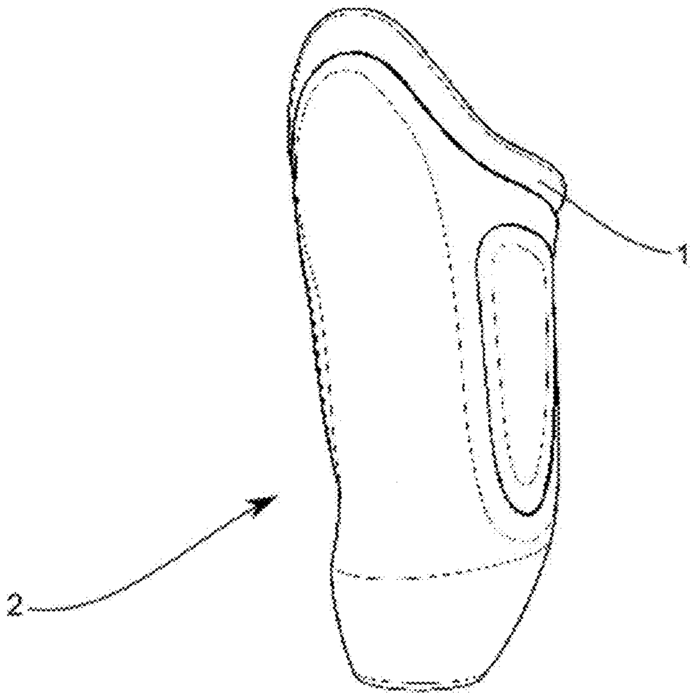
FIG. 8 shows the transfemoral prosthetic socket with the elastic circumferential rim according to the invention.

Transfemoral prosthetic socket (shown in FIG. 8)—the elastic circumferential rim 1 is in contact with the user's lower limb in areas of the hip joint, Scarpa's triangle, adductors, ischial hump, gluteal muscles, wherein the areas with reduced stiffness are usually located in the antero-medial socket part (in the area of Scarpa's triangle, adductors) and in the area around ischial hump.

Figure 10:
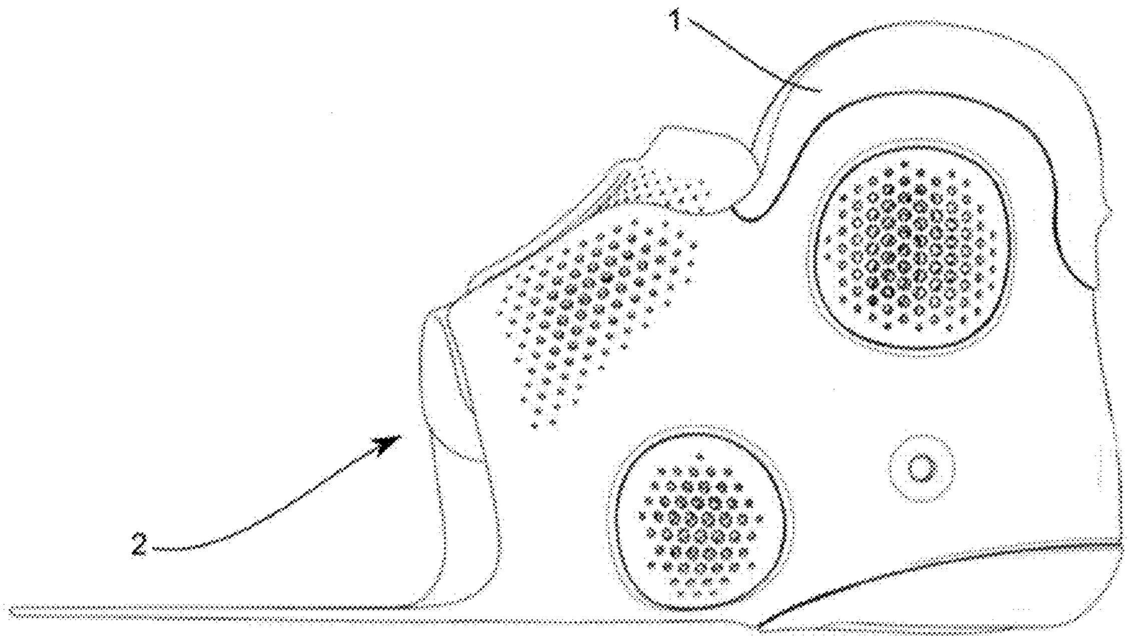
FIG. 10 shows a supramalleolar orthosis with the elastic circumferential rim according to the invention

Supramalleolar orthosis (SMO) (shown in FIG. 10)—the elastic circumferential rim 1 is in contact with the user's lower limb in the areas of the Achilles tendon, ankles, instep, wherein the areas with reduced stiffness are usually located in the ankle areas and upper instep part of the orthosis.

Ankle-foot orthosis (AFO)—the elastic circumferential rim 1 is in contact with the user's lower limb in the areas of the front or back region of the lower leg, ankles, and instep, wherein the areas with reduced stiffness are usually located in the areas of the proximal orthosis edge and upper instep part of the orthosis.

Figure 9:
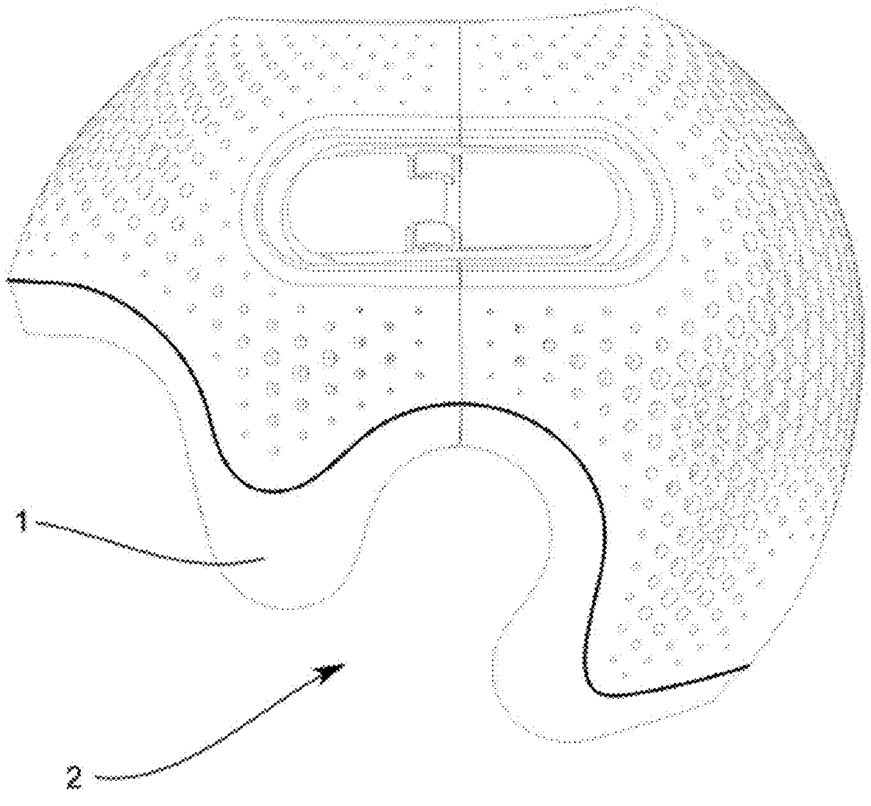
FIG. 9 shows the cranial orthosis with the elastic circumferential rim according to the invention.

Cranial orthosis (CRO) (shown in FIG. 9)—the elastic circumferential rim 1 is in contact with the user's head along the entire circumference of the orthosis, i.e., in the areas of the forehead, cheekbones, areas around the ears and in the back of the neck, wherein the areas with reduced stiffness are usually located in the areas of the back edge of the orthosis and orthosis part around the ears.

Furthermore, the input parameters including data on the dimensions of the users body part and tissue specifics of the user's body part are evaluated in the step of determining the rim 1 areas. Based on the tissue specifics of the users body part, the rim 1 areas corresponding to the sensitive places on the user's body are determined, such as soft tissues, bone prominences, attachments, neural pathways, or vascular supply pathways. Based on the body part dimensions, the tissue specifics of the user's body part can be identified in more detail. In some embodiments, the dimension of the users body part can independently define non-standard shapes in the application site of the prosthetic or orthotic device 2, indicate the size of the bone projections or the length of the bone, therefore the characteristic rim 1 area with adjusted stiffness can be defined purely based on the body part dimensions. Based on data on the dimensions of the user's body part and the tissue specifics of the users body part, the positions, and the sizes of the characteristic rim 1 areas corresponding to the given input parameter about the specific device user are determined. In the step of determining the rim areas, the rim 1 areas are thus defined, including their size and area characteristic of the user's body part with which the parts of the circumferential rim 1 belonging to the given area are in contact.

Subsequently, in the step of determining the area stiffness of the rim 1, the stiffness of the defined rim 1 areas is determined. Firstly, the input data on the overall user status are evaluated, which affect the stiffness of the whole rim 1 or the default rim 1 stiffness is adjusted by them. Furthermore, the stiffness change value in regard to the default rim 1 stiffness or adjusted default rim 1 stiffness based on the data on the overall user status is assigned to the individual rim 1 areas. This is done by assigning the stiffness value change based on the area characteristic of the user's body part, with which the parts of the circumferential rim 1 belonging to the given area are in contact, to all defined rim 1 areas. Some rim 1 parts can belong to more than one rim 1 area, wherein in such case, the stiffness of the rim 1 part is evaluated based on the evaluation of all assigned rim 1 areas together, preferably the resulting stiffness of the rim 1 part is determined based on the most sensitive rim 1 areas which it is part of.

In the first exemplary embodiment, the default rim 1 stiffness represents the highest rim 1 stiffness which, in the step of determining the area stiffness of the rim 1, is only reduced, data on the overall user status can be default, therefore the overall rim 1 stiffness can be reduced by 0 to 50% compared to the default rim 1 stiffness, furthermore, based on the position of the elastic circumferential rim 1 and corresponding anatomic areas of the human body, the area stiffness is reduced by 10 to 50% compared to the default rim 1 stiffness, and based on the dimensions of the user's body part and tissue specifics of the user's body part, the area stiffness is reduced by 10 to 50% compared to the default rim 1 stiffness.

In the step of creating the structural model of the elastic circumferential rim 1, the structural model of the elastic circumferential rim 1 is created based on the step of determining the requirements for stiffness of the elastic circumferential rim 1 and based on the basic structure of the elastic circumferential rim 1 in the software interface. The basic structure of the elastic circumferential rim 1 defines the basic shape and the length of the elastic circumferential rim 1 which correspond to the contours of the prosthetic or orthotic device 2 which are to be provided with the circumferential rim 1. Furthermore, based on the step of determining the requirements for rim 1 stiffness, the stiffnesses of the defined rim 1 areas are adjusted by changing the rim dimensions in these areas. The rim 1 parts which do not belong to any of the rim 1 areas with adjusted stiffness have the default rim 1 stiffness, wherein the transitional areas are located between these parts with default rim 1 stiffness and the areas with adjusted stiffness which ensure the transition between dimensions of the rim 1 with default rim stiffness and dimensions of the rim 1 in the areas with adjusted stiffness. The area stiffness of the rim 1 compared to the default rim 1 stiffness is adjusted by changing the rim 1 width, rim 1 height, or rim 1 width gradient depending on rim 1 height. The rim 1 stiffness adjustment by changing the rim 1 width refers for example also to the rim 1 stiffness adjustment by implementing the cavity into the rim 1 volume. It is preferable in cases where maintaining the certain shape of the rim 1 is preferred and simultaneously the softening of the rim from its inner side oriented toward the user's body is necessary. In the step of the rim structural model, the mechanism for connecting the rim to the device is further determined which is also implemented into the structural model of the elastic circumferential rim.

In the step of manufacturing the elastic circumferential rim 1, the structural model of the elastic circumferential rim 1 is sent to the 3D printer, wherein the 3D printer manufactures the elastic circumferential rim 1 based on the structural model of the elastic circumferential rim 1. Subsequently, the manufactured elastic circumferential rim 1 is connect to the prosthetic or orthotic device 2.

The computer device on which the method of designing and manufacturing the elastic circumferential rim 1 of the prosthetic or orthotic device 2 according to the invention is performed comprises a software application in its memory which includes an interactive configurator of the rim 1. The computer device includes a user input for example in the form of a touch screen, touchpad, mouse and/or keyboard. The interactive configurator of the rim 1 includes a module for selecting the type of the prosthetic or orthotic device 2, a module for importing the dimensions of the prosthetic or orthotic device 2 and a module for collecting data on the device 2 user through which the input parameters are inserted through the user input of the computer device and in which the steps of creating the basic structure of the elastic circumferential rim 1 and determining the position of the elastic circumferential rim 1 are performed. Furthermore, the interactive configurator of the rim 1 includes a module for configurating the rim 1 based on the rim 1 position and data on the device 2 user in which the step of determining the area stiffness of the elastic circumferential rim 1 is performed, a module for adjusting the circumferential rim 1 geometry in which the creation of the structural model of the elastic circumferential rim 1 is performed. The computer device is also communicatively connected to the 3D printer using a cable or a wireless connection.

INDUSTRIAL APPLICABILITY

The invention can also be used in the field of designing and manufacturing the elastic circumferential rims of the different devices and tools intended to be attached on the user's body even outside the field of orthotics and prosthetics.

LIST OF REFERENCE NUMERALS

1—Elastic circumferential rim
2—Prosthetic or orthotic device

The invention claimed is:

1. A method of designing and manufacturing an elastic circumferential rim of a prosthetic or orthotic device comprising the following steps of:

a) creating a basic structure of the elastic circumferential rim based on a type of a prosthetic or orthotic device, wherein a boundary between the elastic circumferential rim and a shell of the prosthetic or orthotic device are defined by a line where stiffness of the prostetic or orthotic device changes abruptly, wherein a stiffness of the elastic circumferential rim is lower than a stiffness of a shell of the prosthetic or orthotic device, b) determining requirements for the stiffness of the elastic circumferential rim in an individual areas along a circumference of the elastic circumferential rim based on dimensions of the prosthetic or orthotic device or at least one data on a device user, c) creating a structural model of the elastic circumferential rim based on the requirements for stiffness of the elastic circumferential rim in the individual areas along the circumference of the elastic circumferential rim and the basic structure of the elastic circumferential rim, wherein the stiffness of the elastic circumferential rim in the individual areas along the circumference of the elastic circumferential rim is adjusted by at least one parameter of a set including rim height, rim thickness, rim thickness gradient depending on the rim height, d) manufacturing the elastic circumferential rim based on the structural model of the elastic circumferential rim.

2. The method of designing and manufacturing the elastic circumferential rim of the prosthetic or orthotic device according to claim 1, wherein the step of manufacturing the elastic circumferential rim is performed using a 3D printing technology.

3. The method of designing and manufacturing the elastic circumferential rim of the prosthetic or orthotic device according to claim 1, wherein the elastic circumferential rim is made of elastomer.

4. The method of designing and manufacturing the elastic circumferential rim of the prosthetic or orthotic device according to claim 1, wherein the step of determining the requirements for stiffness of the elastic circumferential rim includes the steps of determining a position of the elastic circumferential rim on a user's body and a following step of determining an area stiffness of the elastic circumferential rim.

5. The method of designing and manufacturing the elastic circumferential rim of the prosthetic or orthotic device according to claim 4, wherein the step of determining the position of the elastic circumferential rim on the user's body is performed based on the dimensions of the prosthetic or orthotic device and the step of determining the area stiffness of the elastic circumferential rim is performed based on the position of the elastic circumferential rim on the device user's body and at least one data on the device user.

6. The method of designing and manufacturing the elastic circumferential rim of the prosthetic or orthotic device according to claim 1, wherein the requirements for stiffness of the elastic circumferential rim in the individual areas along the circumference of the elastic circumferential rim are determined based on data on a device user including tissue specifics of the device user's body part intended for the prosthetic or orthotic device and at least one data on an overall device user status of a set of user's age, user's weight, user's height, user's activity.

7. The method of designing and manufacturing the elastic circumferential rim of the prosthetic or orthotic device according to claim 1, wherein the stiffness of the elastic circumferential rim in the individual areas along the circumference of the elastic circumferential rim is adjusted using the rim thickness gradient depending on rim height.

8. The method of designing and manufacturing the elastic circumferential rim of the prosthetic or orthotic device according to claim 1, wherein the stiffness adjustment of the elastic circumferential rim in the individual areas along the circumference of the elastic circumferential rim using the rim thickness parameter includes a step of implementing a cavity into at least one area along the circumference of the elastic circumferential rim.

* * * * *